(12) United States Patent
Brantl

(10) Patent No.: US 6,930,093 B2
(45) Date of Patent: *Aug. 16, 2005

(54) USE OF RIBOFURANOSE DERIVATIVES AGAINST INFLAMMATORY BOWEL DISEASES

(75) Inventor: Victor Brantl, Schliengen (DE)

(73) Assignee: Valeant Research & Development, Costa Mesa, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/618,148

(22) Filed: Jul. 10, 2003

(65) Prior Publication Data

US 2005/0009766 A1 Jan. 13, 2005

(51) Int. Cl.$^7$ .................. A61K 31/70; C07H 19/056
(52) U.S. Cl. .................. 514/43; 514/21; 514/235.8; 514/26; 514/378; 514/8; 530/350; 536/28.6; 536/28.7; 536/28.8; 536/23.1; 536/23.5; 544/224; 546/252.1; 546/255; 546/300.1
(58) Field of Search .................. 514/43, 21, 235.8, 514/26, 378, 8; 530/350; 536/28.6, 28.7, 28.8, 23.1, 23.5; 544/224; 546/252.1, 255, 300.1

(56) References Cited

U.S. PATENT DOCUMENTS

| RE29,835 E | 11/1978 | Witkowski et al. |
|---|---|---|
| 5,767,097 A | 6/1998 | Tam |
| 5,907,036 A | 5/1999 | Ramasamy et al. |
| 6,130,326 A | 10/2000 | Ramasamy et al. |
| 6,277,836 B1 * | 8/2001 | Borody ..................... 514/159 |
| 6,455,508 B1 * | 9/2002 | Ramasamy et al. ........... 514/43 |
| 6,518,253 B1 * | 2/2003 | Tam ........................ 514/42 |
| 6,552,183 B1 | 4/2003 | Ramasamy et al. |
| 6,573,248 B2 * | 6/2003 | Ramasamy et al. ........... 514/43 |
| 6,610,665 B1 * | 8/2003 | Bays et al. .................. 514/46 |

OTHER PUBLICATIONS

U. Ruther, et al., "*Herpes–Simplex–Assozierte Exaserbation Eines Morbus Crohn*," Dtsch. Med. Wschr. 117 (1992), 46–50.

Pharamprojects. PJB Publications Ltd., Apr. 2003.

"Target Crohn's and Colitis," Association of the British Pharmaceutical Industry, Feb. 2002.

* cited by examiner

*Primary Examiner*—James O. Wilson
*Assistant Examiner*—Devesh Khare
(74) *Attorney, Agent, or Firm*—Brown Raysman Millstein Felder & Steiner

(57) ABSTRACT

A method for the prophylaxis or treatment of an inflammatory bowel disease is provided, comprising administering to a patient having or at risk of developing an inflammatory bowel disease a therapeutically or preventatively effective amount of one or more ribofuranose derivatives having the Formula (I):

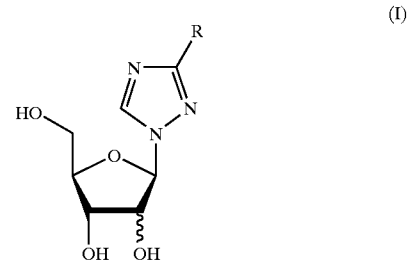

wherein R is a group selected from a carboxamide, an amidine, and pharmaceutically acceptable acid addition salts thereof, and the configuration at the $C_2$ carbon of the ribofuranose moiety is D or L. The one or more ribofuranose derivatives (I) may be used in combination with further active agents such as antivirals or agents effective against inflammatory bowel disease.

16 Claims, No Drawings

USE OF RIBOFURANOSE DERIVATIVES AGAINST INFLAMMATORY BOWEL DISEASES

BACKGROUND OF INVENTION

1. Field of the Invention

This invention relates to a method for treatment and prevention of inflammatory bowel disease which comprises administering an effective amount of a ribofuranose derivative or a pharmaceutically acceptable salt thereof to a mammal. This invention further relates to the use of such compounds in the preparation of a medicament for the treatment and prevention of inflammatory bowel disease.

2. Background of the Invention

Inflammatory bowel disease (IBD) is a term used in the art to generically encompass diseases of the intestine such as ulcerative colitis (UC), irritable bowel syndrome, irritable colon syndrome and Crohn's disease (CD). For many of these diseases, in particular CD, the origin of the disease (bacterial, viral or autoimmune) is unknown. There is sufficient overlap in the diagnostic criteria for UC and CD that it is sometimes impossible to say which a given patient has; however, the type of lesion typically seen is different, as is the localization. UC mostly appears in the colon, proximal to the rectum, and the characteristic lesion is a superficial ulcer of the mucosa; CD can appear anywhere in the bowel, with occasional involvement of stomach, esophagus and duodenum, and the lesions are usually described as extensive linear fissures. IBD is rather common, with a prevalence that is claimed to be in the range of 70–170 in a population of 100,000.

Crohn's disease is currently neither medically nor surgically curable, requiring approaches to treatment that maintains symptomatic control, quality of life, and minimizes short- and long-term toxicity of therapy. The current therapy of IBD usually involves the administration of anti-inflammatory or immunosuppressive agents, such as sulfasalazine, corticosteroids, 6-mercaptopurine/azathioprine, or cyclosporine, which usually bring only partial results. For example, IBD's such as Crohn's disease or ulcerative colitis have been treated in the past with salicylic acid derivatives (such as 5-aminosalicylic acid, also known as 5-ASA or mesalazine; and prodrugs thereof, such as sulfasalazine). Possible side effects of 5-ASA preparations include nausea, vomiting, heartburn, diarrhea and headaches. Other treatments have been based on corticosteroids such as cortisone, however prolonged use of steroids has been known to result in side effects such as weight gain, shrinking of the adrenal glands, gray cataract, glaucoma, osteoporosis and diabetes mellitus. The use of immune modifying drugs such as 6-mercaptopurine and its prodrug azathioprine against Crohn's disease has increased in recent years, but these drugs are slow acting and clinical activity cannot be expected until several weeks or even months of treatment has elapsed. In recent years the use of immuno-modulating monoclonal antibodies that neutralize TNF-α has been contemplated, the only example of such an antibody that obtained marketing approval for use against Crohn's disease currently being infliximab. A drawback of this therapy is the high risk of severe infections when administered by injection and the risk of lymphoproliferative disease. A reported side effect of the treatment with infliximab is bilateral anterior toxic optic neuropathy.

If anti-inflammatory and/or immunosuppressive therapies fail, colectomies are the last line of defense. About 30% of CD patients will need surgery within the first year after diagnosis. In subsequent years, the rate is about 5% per year. Unfortunately, CD is characterized by a high rate of recurrence; about 5% of patients need a second surgery each year after initial surgery. In UC, a further reason for resorting to surgery is that the patients are known to be at much increased risk for developing colorectal cancer, starting 10–15 years after the diagnosis of ulcerative colitis. Presumably this is due to the recurrent cycles of injury to the epithelium, followed by regrowth, increasing the risk of transformation. Accordingly, colostomy is used as prophylaxis against the development of cancer in UC patients.

From the above it is evident that there still exists the need of drugs and therapies that are effective against inflammatory bowel diseases and that avoid the disadvantages of the prior art drugs and treatment.

SUMMARY OF THE INVENTION

One aspect of the present invention provides a method for the prophylaxis or treatment of inflammatory bowel disease (IBD) comprising administering to a patient having or at risk of developing an inflammatory bowel disease a therapeutically or preventatively effective amount of one or more ribofuranose derivatives having the Formula (I):

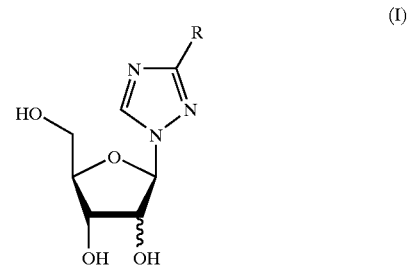

wherein R is a group selected from a carboxamide, an amidine, and pharmaceutically acceptable acid addition salts thereof and the configuration at the $C_2$ carbon of the ribofuranose moiety is D or L.

The method may further comprise administering a compound having Formula (I) in combination with one or more additional agents effective against inflammatory bowel disease including, but not limited to, steroids, corticosteroids, salicylates, immunosuppressants, antibodies and/or antivirals, wherein said compound having Formula (I) and said additional active agent are administered simultaneously in admixture, separately and concomitantly, or successively.

This invention further provides the use of one or more compounds of the Formula (I) alone or in combination with one or more additional active agents effective against inflammatory bowel disease and/or antivirals effective against inflammatory bowel disease in the preparation of a medicament against an inflammatory bowel disease.

This invention further provides a medicament containing one or more ribofuranose derivatives having Formula (I), or a medicament containing one or more ribofuranose derivatives having Formula (I) and at least one compound selected from the group consisting of an antiviral and a further agent effective against inflammatory bowel disease, as a combination for the simultaneous, separate or successive administration against inflammatory bowel disease.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

One aspect of the present invention provides a method for the treatment or prophylaxis of an inflammatory bowel disease, comprising administering to a patient in need thereof one or more compounds generally described by the Formula (I):

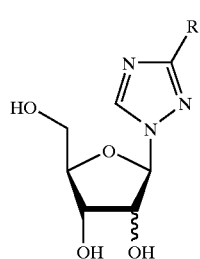

(I)

in a dose range effective to treat or prevent said disease, wherein R is a group selected from a carboxamide, an amidine, and pharmaceutically acceptable acid addition salts thereof and the configuration at the $C_2$ carbon of the ribofuranose moiety is D or L. It is to be understood that any derivatives of Formula (I) that perform the same function as the compounds of Formula (I) are considered the equivalents of the Formula (I).

The numbering of the carbon atoms in the ribofuranose moiety in Formula (I) is such that the carbon bearing the triazole group is 1 (the first carbon atom), and the carbon atom bearing the hydroxymethyl group is 4 (the fourth carbon atom). The configurations at the third and fourth carbon atoms in the ribofuranose moiety are as in ribavirin. The configuration of the $C_2$ carbon atom can be D or L. The configuration of the first carbon atom is not critical to the invention.

Another aspect of this invention is the use of a compound having Formula (I) for the preparation of a medicament against inflammatory bowel disease.

The term "inflammatory bowel disease" as used herein includes all forms of inflammatory processes in the gastrointestinal tissue, including but not limited to, pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome and Crohn's disease; and within Crohn's disease all the subtypes including active, refractory, and fistulizing and Crohn's disease.

The term "against inflammatory bowel disease" as used herein refers to a therapeutic treatment or prophylaxis for inflammatory bowel disease, and an active agent "effective against inflammatory bowel disease" refers to an agent serves in the treatment or prophylaxis of inflammatory bowel disease. An "effective amount" is intended to mean that amount of compound that, when administered to a mammal in need of treatment or prophylaxis, is sufficient to effect treatment or prevention, respectively, of inflammatory bowel disease. The term "treating" is intended to mean at least the mitigation of inflammatory bowel disease in a mammal, such as a human, that is affected, at least in part, by the disease, and includes, but is not limited to, modulating and/or inhibiting the disease condition; and/or alleviating the disease condition. The term "prophylaxis" is intended to mean at least preventing the disease condition from occurring in a mammal, particularly when the mammal is found to be predisposed to having the disease condition but has not yet been diagnosed as having it.

The terms "patient" and "subject" as used herein include any animal, including mammals and humans.

The term "medicament" as used herein includes any type of medicament for oral, nasal, topical, transdermal, rectal and parenteral administration (e.g., administration by injection), whereby the medicament can be a single dosage containing one or more ribofuranose derivatives having Formula (I) alone or in admixture with at least on additional agent effective against inflammatory bowel disease, or one or more ribofuranose derivatives having Formula (I) and at least on additional agent effective against inflammatory bowel disease in separate dosage forms. Additionally, the term "medicament" includes a kit with one or more dosage forms containing one or more ribofuranose derivatives having Formula (I) and separately at least one dosage form containing at least one additional agent effective against inflammatory bowel disease, or a kit with one or more dosage forms containing one or more ribofuranose derivatives having Formula (I) alone or in admixture with one or more additional agents effective against inflammatory bowel disease and one or more separate dosage forms containing either the ribofuranose derivative having Formula (I) or an additional agent effective against inflammatory bowel disease.

Examples of ribofuranose derivatives having Formula (I) used in the compositions, medicaments, and methods according to the invention include:

(1) Ribavirin (1-β-D-ribofuranosyl-1H-1,2,4-triazole-3-carboxamide), which is the compound having Formula (I) where R is (C=O)NH$_2$), or a pharmaceutically acceptable acid addition salt thereof;

(2) Levovirin™ (1-β-L-ribofuranosyl-1H-1,2,4-triazole-3-carboxamide), which is the compound having Formula (I) where R is (C=O)NH$_2$), or a pharmaceutically acceptable acid addition salt thereof. This is the L-form of Ribavirin and its synthesis is disclosed in U.S. Pat. No. 6,130,326, which is specifically incorporated herein by reference;

(3) 1-β-D-ribofuranosyl-1H-1,2,4-triazole-3-amidine, which is the compound having Formula (I) where R is (C=NH)NH$_2$), or a pharmaceutically acceptable acid addition salt thereof;

(4) 1-β-L-ribofuranosyl-1H-1,2,4-triazole-3-amidine, which is the compound having Formula (I) where R is (C=NH)NH$_2$, or a pharmaceutically acceptable acid addition salt thereof; and (5) any mixture of compounds (1)–(4).

Preferred ribofuranose derivatives having Formula (I) include 1-β-D-ribofuranosyl-1H-1,2,4-triazole-3-carboxamide, 1-β-L-ribofuranosyl-1H-1,2,4-triazole-3-carboxamide, the hydrochloric acid addition salt of 1-β-D-ribofuranosyl-1H-1,2,4-triazole-3-amidine (D-Viramidine®), and the hydrochloride salt of 1-β-L-ribofuranosyl-1H-1,2,4-triazole-3-amidine (L-Viramidine®). D- and L-Viramidine® are prodrugs of Ribavirin and are disclosed in U.S. Pat. No. RE029835, which is specifically incorporated herein by reference.

The term "pharmaceutically acceptable acid addition salt" refers to a compound obtained upon treatment of a compound having Formula (I) with any pharmaceutically acceptable acid, including, but not limited to, hydrochloric, hydrobromic, acetic, propionic, p-toluenesulfonic, sulfuric, nitric or lactic acid. Methods of preparing acid addition salts of such compounds are well known to those skilled in the art. One example of such a method is described in U.S. Pat. No. 6,455,408 B1, which is incorporated herein by reference.

When an acid addition salt of the compound having Formula (I) is intended for administration by injection, the amount of acid added to the compound having Formula (I) in the preparation of the salt may be restricted by the pH of the aqueous solution of the resulting acid addition salt, which should be within physiologically tolerable ranges.

In certain cases, where the composition or medicament contains one or more further agents and/or antivirals active against inflammatory bowel disease that contain an acidic hydrogen, a "pharmaceutically acceptable salt" of the additional agents and/or antivirals may be formed by deprotonation of the acidic hydrogen. Such deprotonation salts include, for example, the sodium or potassium salts of acyclovir and valacylovir, obtained by deprotonation of the 1-imino hydrogen. Other methods for preparing salts of agents containing an acidic hydrogen are well known in the art.

One embodiment of this invention comprises a method of treating or preventing inflammatory bowel disease in a patient, comprising administering a therapeutically effective or preventatively effective amount of one or more ribofuranose derivatives having Formula (I) or the acid addition salts thereof to a patient in need thereof. The amount of ribofuranose derivative having Formula (I) that is effective for the treatment or prevention of an inflammatory bowel disease will vary depending on the compound used and on other factors such as the body weight of the subject and may be determined by clinical studies on laboratory animals or on human volunteers. An indication that a therapeutically effective in vivo amount was used is the induction of a clinical remission of the inflammatory bowel disease in question. It is well within the ordinary skill of the art to modify the route of administration and dosage regimen in order to manage the pharmacokinetics of the present compounds for maximum beneficial effect in patients.

An exemplary dosage regime for a ribofuranose derivative having Formula (I) may be, when administered orally for the treatment or prophylaxis of inflammatory bowed disease, in the range of 100 mg to 4 g per day over a period of 1 to 4 weeks. This dosing regime is especially suitable for the administration of Ribavirin, and in particular for the administration of Ribavirin for the treatment or prophylaxis of Crohn's disease. With the lower doses within the range of 100 mg to 1.5 g per day the treatment may be extended to up to six months, in particular for prophylactic treatment.

An exemplary dosage regime for a ribofuranose derivatives having Formula (I), when administered as injectable intravenous solution for treatment of acute or subacute inflammatory bowel disease, is:

a) initial administration of a loading dose of about 10 to about 40 mg/kg body weight of the patient, over a period of about 20 to about 45 minutes;

b) administration of subsequent doses of about 5 to about 25 mg/kg body weight, in intervals of about 4 to about 6 hours, for the first 4 days, starting one such interval after the end of administering the loading dose of step a); and c) administration of subsequent doses of about 2 mg to about 15 mg/kg body weight, in intervals of about 6 hours to about 10 hours, for the next 3 days, starting one such latter interval after the end of the regime of step b). This dosing regime is especially suitable for the administration of Ribavirin, and in particular for the administration of Ribavirin for the treatment or prophylaxis of Croim's disease.

An exemplary dosing regime for the intravenous administration of Ribavirin according to this invention for the treatment or prophylaxis of an inflammatory bowel disease is provided in Table 1.

TABLE 1

| Day | Time (hours) | | | |
| --- | --- | --- | --- | --- |
| | 0 | 6 | 12 | 18 |
| 1 | Loading dose (33 mg/kg) | 16 mg/kg | 16 mg/kg | 16 mg/kg |
| 2 | 16 mg/kg | 16 mg/kg | 16 mg/kg | 16 mg/kg |
| 3 | 16 mg/kg | 16 mg/kg | 16 mg/kg | 16 mg/kg |
| 4 | 16 mg/kg | 16 mg/kg | 16 mg/kg | 16 mg/kg |
| | 0 | 8 | 16 | |
| 5 | 8 mg/kg | 8 mg/kg | 8 mg/kg | |
| 6 | 8 mg/kg | 8 mg/kg | 8 mg/kg | |
| 7 | 8 mg/kg | 8 mg/kg | | |

In one embodiment, the compound having Formula (I) is Ribavirin. Since Ribavirin has been on the market for several years, many dosage forms and routes of administration are known, and all appropriate dosage forms and routes of administration may be utilized. For example, in addition to oral administration, ribavirin may given intravenously, intramuscularly, intraperitoneally, topically, and the like, all of which are known.

A compound having Formula (I), whether alone or in the combination therapies or preventions as discussed herein, may be administered in any appropriate pharmaceutical formulation, and under any appropriate protocol. Thus, administration may take place by various routes including oral (for example as tablets, lozenges, hard or soft capsules, aqueous or oily suspensions, emulsions, dispersible powders or granules, syrups or elixirs), parenteral (including subcutaneous injections, intravenous, intramuscular, by intrastemal injection or infusion techniques), transdermal (for example as a patch which may include a penetration enhancement agent), by inhalation spray (such as in the form of a finely divided powder with an appropriate powdery diluent or a liquid aerosol, to form an ordered mixture that can be inhaled with a dry powder inhaler; or as an aerosolizable solution, to be inhaled e.g. with a metered dose inhaler, for administration by insufflation (for example as a finely divided powder), for topical use (for example as creams, ointments, gels, or aqueous or oily solutions or suspensions), buccal and suppository administration, and other routes of administration, and in dosage unit formulations containing conventional non-toxic pharmaceutically acceptable carriers, adjuvants, and vehicles.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose. methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 $\mu$m or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Another formulation employed in the methods of the present invention employs transdermal delivery devices, patches, bandages, and the like. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, the disclosure of which is herein incorporated by reference. Such patches may be constructed for continuous, pulsatile, or on demand delivery of pharmaceutical. For example, a dose of a ribofuranose derivative having Formula (I) may be combined with skin penetration enhancers, such as propylene glycol, polyethylene glycol, isopropanol, oleyl alcohol, ethoxydiglycol, sodium xylene sulfonate, ethanol, oleic acid, N-methylpyrrolidone, laurocapram, alkanecarboxylic acids, dimethylsulfoxide, polar lipids, and N-methyl-2-pyrrolidone, and the like, which increase the permeability of the skin to the dose of ribofuranose derivative having Formula (I) and permit the dose of ribofuranose derivative having Formula (I)to penetrate through the skin and into the bloodstream. A patch comprising a ribofuranose derivative having Formula (I) may further comprise one or more agents such as moisturizers, humectants, oils, emulsifiers, thickeners, thinners, surface active agents, fragrances, preservatives, antioxidants, vitamins, or minerals. The ribofuranose derivative having Formula (I) may also be further combined with a polymeric substance, such as ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch. The backing can be any of the conventional materials such as polyethylene, ethyl-vinyl acetate copolymer, polyurethane and the like.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The administration of a compound having Formula (I), alone or in combination with another active ingredient as described herein, need not be restricted to a single daily injection, but may include alternative frequencies and routes. For example, where relatively high amounts of a compound having Formula (I) need to be delivered, two to four or more daily injections are contemplated. Similarly, where high plasma concentrations of a compound having Formula (I) are desired over an extended period, a permanent delivery is contemplated. For example, a more permanent delivery may include the use of a continuous infusion, an osmotic pump, or a sustained release implant.

With respect to dosage of a compound having Formula (I), whether alone or in combination with one or more additional agents against inflammatory bowel disease, one of ordinary skill in the art will recognize that a therapeutically effective amount will vary with the infection or condition to be treated, its severity, the treatment regimen to be employed, the pharmacokinetics of the agent used, as well as the patient (animal or human) treated. It is further contemplated that while treatment success may be achieved at relatively low plasma concentrations of the compounds having Formula (I), other conditions may require relatively high dosages.

In embodiments wherein the compound having Formula (I) is administered together in admixture, separate and simultaneously or successively with one or more additional active agents and/or antivirals effective against inflammatory disease, it is well within the skill of those of ordinary skill in the art to decide, depending on the type of ribofuranose derivative having Formula (I) and the type of further active agent and/or antiviral to be co-administered, what type of administration route to choose for each compound. It is further within the skill of one of ordinary skill in the art to determine whether the compound having Formula (I) and the one or more additional active agents and/or antivirals a can be co-formulated into one single composition or whether, for example due to some incompatibility, they should be formulated into separate dosage forms to then be used as a kit, or administered independently but concomitantly or successively according to the respective dosing regimes. Likewise the proper choice of excipients and/or diluents is within the knowledge of the skilled person, particularly as the ribofuranose derivatives having Formula (I) and the further active agents per se are known compounds that have been previously used in other therapies and indications.

Because the ribofuranose derivatives having Formula (I) are water soluble, they can be administered in the form of an injectable, especially intravenous solution in a pharmaceutically acceptable solvent, such as water for injection (WFI) or physiological saline solution, preferredly buffered to a pH of about 5.0 to bout 7.5, and optionally by using suited pharmaceutically acceptable cosolvents such as ethanol or DMSO. Conventional buffers such as phosphates, bicarbonates or citrates can be used for buffering. These solutions may be prepared immediately prior to use.

In a further embodiment, this invention provides a method of treatment or prophylaxis of inflammatory bowel disease in a patient comprising administering at least one derivative having Formula (I) in combination with one or more agents effective against inflammatory bowel disease. Combination therapies according to the present invention comprise the administration of at least of compound having Formula (I) or an acid addition salt thereof and at least one other pharmaceutically active ingredient. In this method, a compound having Formula (I) may be administered in admixture or separately with another active agent against inflammatory bowel disease, and when administered separately this may occur simultaneously or separately in any order. The amounts of the active agent(s) and the compound having Formula (I) and the relative timings of administration will be selected in order to achieve the desired combined therapeutic effect.

As stated, one embodiment of this invention for the treatment or prophylaxis of inflammatory bowel disease comprises administering one or more derivatives having Formula (I) in an amount effective to treat or prevent the disease. Alternatively, the ribofuranose derivative having Formula (I) can be co-administered and/or co-formulated with further active agents effective against inflammatory bowel disease including, but not limited to:

(a) conventional agents used in the field of treatment of inflammatory bowel diseases including, but not limited to, anti-inflammatories (e.g. steroids and corticosteroids such as cortisone and hydrocortisone, salicylates such as mesalazine and sulfasalazine, and cytokines), immunosuppressants such as mercaptopurine, azathioprine, metothrexate, cyclosporine and tacrolimus, and antibodies including active fragments thereof, such as the immunomodulating monoclonal antibody against TNF-α known as infliximab; and/or (b) further antivirals different from the ribofuranose derivative having Formula (I) including, but not limited to, abacavir, acyclovir, acyclovir sodium, acyclovir potassium, adefovir, amantadine, amprenavir, atazanavir, brivudine, capravirine, cidofovir, delavirdine, didanosine, efavirenz, emivirin, emtricitabine, enfurvirtide, famciclovir, fosamprenavir, foscarnet, ganciclovir, idoxuridine, indinavir, lamivudine, lopinavir, memantine, mozenavir, nelfinavir, nevirapine, oseltamivir, penciclovir, rimantidine, pentafuside, ritonavir, saquinavir, stavudine, tenofovir, tipranavir, trifluridine, valaciclovir, valganciclovir, zalcitabine, zanamivir, zidovudin, and the pharmaceutically acceptable salts thereof and mixtures thereof, and/or (c) additional agents for the treatment of inflammatory bowel disease including, but not limited to, humanized monoclonal antibody against TNF-α, flavonoids, monoclonal antibodies against IL-12 or IL-6, monoclonal antibodies against the α4β7 integrin receptor, keratinocyte growth factor, protein inhibitors of TNF-α, glucocorticoids, peptide analogues of glucagon-like peptide-2, glutathione peroxidase mimics, anti-sense TNF inhibitors, anti-sense ICAM-1 inhibitor, nitric oxide-releasing steroid derivatives, analogues of GLP-2, neurokinin-1 antagonists, NF-kappa-B inhibitors, orally-active phosphodiesterase IV inhibitors, thiazole derivatives, 5-lipoxygenase inhibitors, L-selectin antagonists, enzyme inhibitors (e.g., tryptase inhibitors), immunosuppressive macrolides, glutathione peroxidase mimics, interferon, omega-3 fatty acids, inhibitors of cytokine synthesis, bactericidal/permeability-increasing (BPI) agents, guanyl-hydrozone compounds, apoptotic anti-neoplastic drugs, thalidomide, and recombinant interleukin-11. Non-limiting examples of such compounds are listed in Table 2.

TABLE 2*

| Company | Product Name | Product Type/Comments |
|---|---|---|
| AstraZeneca | Budesonide | Synthetic steroid |
| Ferring Pharmaceuticals | Mesalazine | Microsphere formulation of 5-aminosalicylate |
| Provalis Procter & Gamble | Mesalazine | pH-sensitive coated form of 5-aminosalicylate |
| Pharmacia | Olsalazine | Salicylate |
| Shire Pharmaceuticals | Balsalazide | Salicylate |
| Pharmacia Wyeth | Methotrexate | Immunosuppressive agent |
| GlaxoSmithKline | Azathioprine 6-mercaptopurine | Immunoactive and immunosuppressive agents |
| Novartis | Cyclosporin | Immunosuppressive agent |
| Schering Plough | Infliximab | Humanized monoclonal antibody against TNF-α |
| Dong-A | DA-6034 | Flavonoid |
| Abgenix | ABX-IL8 | Monoclonal antibody against IL-12 |
| Chugai | MRA (anti-IL-6) | Humanized monoclonal antibody against IL-6 for IBD |
| Nobex | Apaza | Orally-active drug targeting the lower GI tract which combines anti-inflammatory and immunomodulatory properties |
| Tripep | TNF-Alpha inhibitor | Protein polymerization inhibitor that inhibits TNF-α |
| GlaxoSmithKline | SB-281832 | p38 kinase inhibitor (for IBD) |
|  | SB-683698 | Anti-inflammatory inhibitor of α4 integrin (for IBD) |
|  | Repifermin | Keratinocyte growth factor (for IBD) |
| IVAX | Etiprednol dicloacetate (EPDC) | Orally-active glucocorticoid, rapidly converted to its inactive form after absorption. |
| NPS Pharmaceuticals | ALX-0600 | 33-amino-acid peptide analogue of glucagon-like peptide-2 (GLP-2). |
| OXIS Pharmaceuticals | BXT-51702 | A small molecule glutathione peroxidase mimic. Accelerates metabolism of peroxides, is a potent inhibitor of NF-κB, prevents oxidative damage and downregulates the inflammatory response. |
| ISIS Pharmaceuticals | ISIS 104838 | Anti-sense TNF inhibitor |
|  | ISIS 2302 | Anti-sense ICAM-1 inhibitor (for IBD) |
| NiCox SA | NiCox 456 | NO-releasing mesalazine (for IBD) |
|  | NiCox 1015 | NO-releasing prednisolone derivative (for IBD) |
| Protherics | CytoAb | Protein inhibitor of TNF |
| Pfizer | C 96348 | Antagonist of neurokinin-1 (NK-1) |
| Phytopharm plc | P54 | NF-kappa-B inhibitor (for IBD) |
| Tanox Inc | TNX-100 | Monoclonal antibody inhibitor of CD40 |
| Celgene | CDC-801 | Lead compound from a series of small, orally-active phosphodiesterase IV inhibitors (SelCID; Selective Cytokine Inhibitory Drugs). |
|  | Thalidomide | TNF inhibitor |
| Otsuka | OPC-6535 | Lead compound in a series of non-peptidic, thiazole derivatives, acting as an inhibitor of superoxide production by human neutrophils |
| SangStat Corporation | RDP-58 | Orally-active peptide inhibitor of TNFα mRNA translation. It prevents translation of the TNF protein rather than binding to the protein to inhibit function. |
| Cantabria | AM-24 | 5-lipoxygenase inhibitor and L-selectin antagonist |
| Abbott (joint development with Cambridge Antibody Technology plc) | D2E7 | Human monoclonal antibody against TNFα |
|  | J695 | Human monoclonal antibody against IL-12 |
| Axys Pharmaceuticals | APC-2059 | Enzyme (tryptase) inhibitor (for IBD) |
| Fujisawa | FK506 (tacrolimus) | Immunosuppressive macrolide |
| Millenium | MLN-02 | Humanized monoclonal antibody to the a4β7 integrin receptor (for IBD) |
| Oxis Pharmaceuticals | GPx | Glutathione peroxidase mimic (in UC) |
| Serono | IFN-beta-1a | Interferon (cytokine) for IBD |
|  | rTBP-1 | Protein inhibitor of TNF |
| Astra Zeneca | Rofleponide | Oral steroid with topical action (for IBD) |
| Celltech | CDP 870 | 3rd generation PEG humanized anti-TNFα antibody fragment |
|  | CDP 571 | Fully humanized monoclonal antibody against TNFα |
| Alizyme | ATL-2502 | Steroid derivative in special colonic delivery formulation |

TABLE 2*-continued

| Company | Product Name | Product Type/Comments |
|---|---|---|
| Elan Corporation | Natalizumab | Humanized monoclonal antibody against α4 integrin |
| Inkine Pharmaceuticals | CBO-1011 | Steroidal molecule |
| Schering Plough | Tenovil (IL-10) | Anti-inflammatory cytokine |
| Tillotts Pharma | EPA DHA | Enteric coated form of purified fish oil containing free fatty acid forms of eicosapentaenoic acid (EPA) and docosahexaenoic-omega-3 acid DHA |
| Xoma | rBPI21 (Neuprex ™) | A recombinant bactericidal/permeability-increasing (BPI) protein. Kills gram-negative bacteria and neutralizes the bacterial endotoxin |
| Cytokine Pharma Sciences | CNI-1493 | A synthetic guanylhydrazone compound, Inhibits the synthesis of inflammatory cytokines such as TNF-α and IL-1 |
| Cell Pathways | CP-461 | A Selective Apoptotic Antineoplastic Drug (SAAND). Induces apoptosis in neoplastic cells by inhibiting cyclic guanosine monophosphate phosphodiesterase (cGMP PDE) |
| Wyeth-Ayerst Research | rhIL-11 | A recombinant human interleukin-11. Affects class II antigen processing and colonic epithelial cell proliferation and metabolism |

*Sources: Pharmaprojects, PJB Publications Ltd., status: April 2003; Target Crohn's and Colitis, Information Booklet published by the Association of the British Pharmaceutical Industry, status: February 2002); FDA at www.clinicaltrials.gov, status: April 2003).

In any of the medicaments described herein, a compound having Formula (I) may further be co-used with infliximab, wherein the compound having Formula (I) and infliximab can be administered together or separately.

Non-limiting examples of combinations of the ribofuranose derivative having Formula (I) with other active agents against inflammatory bowel disease according to this invention include the following:

(i) one or more derivatives having Formula (I) with one or more compounds of list (a) and/or with one or more antivirals such as those selected from list (b) and/or with one or more compounds of list (c); and (ii) a combination as described in (i), additionally with infliximab.

Preferably, the medicaments against inflammatory bowel disease according to this invention may contain a combination of a ribofuranose derivative of Formula (I) and one or more further active agents selected from any of the above lists (a), (b) and (c). In this embodiment, the ribofuranose derivative of Formula (I) and the one or more further active agents are intended for simultaneous, separate or successive administration.

The medicaments of this invention can be formulated of any type of administration to a subject, including, but not limited to, intravenous, parenteral, oral, inhalation, topical, transdermal, or rectal administration, continuous infusion, or administration with an osmotic pump or a sustained release implant.

In one preferred embodiment of a medicament of this invention, the ribofuranose derivative having Formula (I) comprises at least one ribofuranose derivative selected from the group consisting of 1-β-D-ribofuranosyl-1H-1,2,4-triazole-3-carboxamide, 1-β-L-ribofuranosyl1H-1,2,4-triazole-3-carboxamide, 1-β-D-ribofuranosyl-1H-1,2,4-triazole-3-amidine, 1-β-L-ribofuranosyl-1H-1,2,4-triazole-3-amidine, and pharmaceutically acceptable acid addition salts thereof such as the hydrochloric acid addition salt of 1-β-D-ribofuranosyl-1H-1,2,4-triazole-3-amidine and the hydrochloric acid addition salt of 1-β-L-ribofuranosyl-1H-1,2,4-triazole-3-amidine. The medicaments of this invention are suitable for treating or preventing inflammatory diseases including, but not limited to, pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome and Crohn's disease. A preferred medicament for the treatment of Crohn's disease comprises 1-β-D-ribofuranosyl-1H-1,2,4-triazole-3-carboxamide, wherein the Crohn's disease includes active Crohn's disease, refractory Crohn's disease, and fistulizing Crohn's disease.

One exemplary medicament of this invention comprises a ribofuranose derivative having Formula (I) in an amount between about 100 mg and 1.5 grams.

Other preferred combinations and medicaments include 1-β-D-ribofuranosyl-1H-1,2,4-triazole-3-carboxamide in admixture with acyclovir and 1-β-L-ribofuranosyl-1H-1,2,4-triazole-3-carboxamide in admixture with acyclovir.

In the embodiment wherein one or more agents used in the field of treatment of inflammatory bowel diseases such as those of list (a) are co-used with one or more derivatives having Formula (I), they may be administered in therapy and/or co-formulated in an amount or dosage from about the same to about half the dosage that would, when used without the ribofuranose derivative having Formula (1), be effective to bring about a reduction in the expression of proinflammatory cytokines (such as TNF-α, TNF-β, INF-γ, IL-2, IL-12) in the serum or in a tissue sample of the intestine mucosa of the subject to be treated.

In the embodiment wherein one or more antivirals such as those of list (b) are co-used with one or more derivatives having Formula (I), they may be administered in therapy or prevention and/or co-formulated in an amount or dosage which is from about the same to about half the dosage that would, when used without a compound having Formula (I), be effective, in case an ordinary viral infection, to promote an observable (e.g. by RT-PCR) reduction in virus load and/or propagation.

In the embodiment wherein one or more active agents against inflammatory bowel disease such as those of list (c) are co-used with one or more derivatives having Formula (I), they may be administered in therapy and/or be co-formulated in an amount or dosage which is from about the same to about half the dosage that would, when used without ribofuranose derivative having Formula (I), be effective in promoting its respective functional effect, which effect and corresponding assaying technique is described in the respective compound's medicament information and/or drug master file.

To prepare the pharmaceutical compositions according to the present invention, a therapeutically effective or prophylactically effective amount of one or more derivatives having Formula (I) (as well as a compound provided in list (a), (b), or (c) if co-used with the compound having Formula (I)) is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples include excipients such as stabilizers (to promote long term storage), emulsifiers, binding agents, thickening agents, salts, preservatives, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the ribavirin, its use in the therapeutic compositions and preparations is contemplated. Supplementary active ingredients can also be incorporated into the compositions and preparations as described herein.

In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

In the case of the combination therapies the ribofuranose derivative having Formula (I) and an additional active agent against inflammatory bowel disease such as those of lists (a), (b), and (c), the compound having Formula (I) and the additional active agent may be formulated in admixture into one single dosage. Alternatively they may be formulated in separate dosage forms for the simultaneous, separate or sequential use of the two types of dosage forms and/or to be provided as a medication kit with appropriate directions of use.

The invention will now be illustrated in further detail by the following non-limiting examples.

EXAMPLE 1

Formulation of an injectable solution

| Ingredient | Content (per ml solution) | Function |
| --- | --- | --- |
| ribavirin | 100 mg | agent effective against inflammatory bowel disease |
| Na$_2$HPO$_4$ anhydr. Ph. Eur. | 0.369 mg | buffer |
| KH$_2$PO$_4$ | 8.718 mg | buffer |
| 0.1 M HCl or 0.1 M NaOH | q.s. | adjust pH of solution to 5.4–5.6 |
| WFI Ph. Eur. | ad 1 ml | solvent |

EXAMPLE 2

Ribavirin Assay in a DNBS (2,4 dinitrobenzenesulfonic Acid) Induced Distal Colitis in Wistar Rats as a Model for Inflammatory Bowel Disease in Humans Animals Wistar derived female rats were provided by MDS Pharma Services Taiwan Ltd. and housed in APEC$^R$ cages. All animals were maintained in a controlled temperature (22° C.–24° C.) and humidity (60–80%) environment with 12 hours light dark cycles for at least one week in the laboratory prior to use. Free access to standard lab chow (LabDiet, Rodent Diet, PMI Nutrition International, USA) and tap water was granted. All aspects of the work including housing, experimentation and disposal of animals were performed in general accordance with the International Guiding Principles for Biomedical Research Involving Animals (CIOMSI Publication No. ISBN 9290360194, 1985).

Chemicals

DNBE (TCI, Japan), absolute ethanol (Merck, Germany), sodium chloride (Wako, Japan), sulfasalazine (Sigma, USA) and Tween 80 (Wako, Japan).

Assay

Groups of 3 Wistar derived female rats weighing 180±20 grams and fasted for 24 hours were used. Distal colitis was induced by intra-colonic instillation of 2,4-ninitrobenzene sulfonic acid (DNBS; 30 mg in 0.5 mL ethanol 30%), which was followed by injection of air (2 mL) through a cannula to ensure that the solution remained in the colon. Test substances (ribavirin 100 mg/kg or sulfalazine 300 mg/kg) plus vehicle (2% Tween 80 in water) were administered p.o. 24 and 2 hours before DNBS instillation and then daily for 5 days. Two control groups were similarly treated with vehicle alone while challenged with either DNBS (vehicle-control) or 0.9% NaCl solution (blank-control). The animals were sacrificed 24 hours after the final dosing of test compound and each colon was removed and weighed. During the experiment, the presence of diarrhea was recorded daily. Furthermore, when the abdominal cavity was opened, adhesions between the colon and other organs were first noted; presence of colonic ulceration was evaluated after removal and weighing of each colon. The colon-to-body weight (BW) ratio was then calculated for each animal according to the formula: Colon [(g)/BW(g)]×100%. The "Net" increase in the ratio of vehicle-control+DNBS group relative to vehicle-control group was used as a base for comparison with test substance treated groups and expressed as percent decrease. A 30% or more ($\geq$30%) reduction in colon-to-body weight ratio, relative to the vehicle-treated control group, is considered significant. The numerical data and results of the assay are given in Table 3. The data presented in Table 3 demonstrate that Ribavirin is effective in this IBD model.

TABLE 3

| Treatment | Dose | N | B.W. (g) Day 1 | Colon (g) Day 8 | Colon weight per 100 g B.W. | I |
|---|---|---|---|---|---|---|
| Blank-Control (2% Tween 80) | 10 mL/kg × 7 | 1 | 170 | 190 | 0.49 | 0.258 |
| | | 2 | 170 | 190 | 0.56 | 0.295 |
| | | 3 | 170 | 190 | 0.51 | 0.268 |
| | | Avg | 170 | 190 | 0.52 | 0.274 |
| Vehicle-Control (2% Tween 80) | 10 mL/kg × 7 | 1 | 170 | 145 | 1.38 | 0.952 |
| | | 2 | 180 | 155 | 1.09 | 0.703 |
| | | 3 | 180 | 145 | 1.27 | 0.876 |
| | | Avg | 177 | 148 | 1.25 | 0.844 |
| Ribavirin | 100 mg/kg × 7 | 1 | 180 | 150 | 1.17 | 0.780 |
| | | 2 | 190 | 155 | 0.96 | 0.619 |
| | | 3 | 180 | 155 | 1.24 | 0.800 |
| | | Avg | 183 | 153 | 1.12 | 0.733 |
| Sulfasalazine | 300 mg/kg × 7 | 1 | 185 | 160 | 1.01 | 0.631 |
| | | 2 | 180 | 155 | 0.85 | 0.548 |
| | | 3 | 185 | 155 | 1.08 | 0.697 |
| | | Avg | 183 | 157 | 0.98 | 0.625 |

EXAMPLE 3

Intravenous infusion solution

| Ingredient | Content (per 100 ml infusion solution) | Function |
|---|---|---|
| Solution 1: | | |
| ribavirin | 100 mg | agent effective against inflammatory bowel disease |
| WFI Ph. Eur. | ad 100 ml | solvent |
| Solution 2: | | |
| acyclovir sodium | 109.8 mg | Further agent effective against inflammatory bowel disease |
| WFI Ph. Eur. | ad 100 ml | solvent |
| Final infusion solution: | | |
| Solution 1 | 100 ml | |
| Solution 2 | 100 ml | |

Solution 1 and 2 are mixed immediately prior to use.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treatment [or prophylaxis] of an inflammatory bowel disease in a subject in need of said treatment [or prophylaxis], said method comprising:

providing one or more ribofuranose derivatives having the Formula (I):

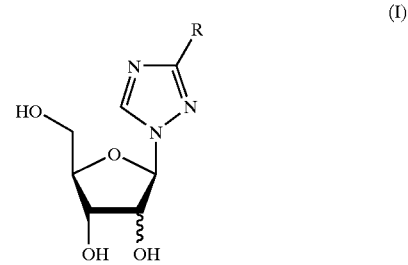

wherein R is a group selected from the group consisting of a carboxamide, an amidine and pharmaceutically acceptable acid addition salts thereof and the configuration at the $C_2$ carbon of the ribofuranose moiety is [D or] L; and administering said one or more ribofuranose derivatives to said subject in an amount effective to treat [or revent] said inflammatory bowel disease.

2. The method of claim 1, wherein the ribofuranose derivative having the Formula (I) comprises at least one derivative selected from the group consisting of [1-β-D-ribofuranosyl-1H-1,2,4-triazole-3-carboxamide,] 1-β-L-ribofuranosyl-1H-1,2,4-triazole-3-carboxamide, [1-β-ribofuranosyl-1H-1,2,4-triazole-3-amidine,] 1-β-L-ribofuranosyl-1H-1,2,4-triazole-3-amidine, pharmaceutically acceptable acid addition salts thereof.

3. The method of claim 2, wherein the ribofuranose derivative having Formula (I) is 1-β-L-ribofuranosyl-1H-1,2,4-triazole-3-carboxamide.

4. The method of claim 2, wherein the ribofuranose derivative having Formula (I) is 1-β-L-ribofuranosyl-1H-1,2,4-triazole-3-amidine.

5. The method of claim 2, wherein the ribofuranose derivative is the hydrochloric acid addition salt of 1-β-L-ribofuranosyl-1H-1,2,4-triazole-3-amidine.

6. The method of claim 1, wherein the ribofuranose derivative having Formula (I) is provided in combination with an antiviral, wherein the ribofuranose derivative having Formula (I) and the antiviral are administered to said subject simultaneously as an admixture, separately and simultaneously, or separately in any order.

7. The method of claim 6, wherein said antiviral agent is selected from the group consistin of abacavir, acyclovir, acyclovir sodium, acyclovir potassium, adefovir, amantadine, amprenavir, atazanavir, brivudine, capravirine, cidofovir, delavirdine, didanosine, efavirenz, emivirin emtricitabine, enfurvirtide, famciclovir, fosamprenavir, foscarnet, ganciclovir, idoxuridine, indinavir, lamivudine, lopinavir, memantine, mozenavir, nelfinavir, nevirapine, oseltamivir, penciclovir, rimantidine, pentafuside, ritonavir, saquinavir, stavudine, tenofovir, tipranavir, trifluridine, valaciclovir, valganciclovir, zalcitabine, zanamivir, zidovudin, and the pharmaceutically acceptable salts thereof and mixtures thereof.

8. The method of claim 6, wherein the ribofuranose [derivatives are 1-β-D-ribofuranosyl-1H-1,2,4-triazole-3-carboxamide and] derivative is 1-β-L-ribofuranosyl-1H-1,2,4-triazole-3-carboxamide and the antiviral is acyclovir.

9. The method of claim 1 or 6 further comprising providing one or more further agents effective against an inflammatory bowel disease for simultaneous or successive administration with aid derivative having Formula (I), wherein said further active agent is selected from the group consisting of anti-inflammatories, immunosuppressants, antibodies, antibody fragments, humanized monoclonal antibody against TNF-α, flavonoids, monoclonal antibodies against IL-12, monoclonal antibodies against IL-6, monoclonal antibodies against the α4β7 integrin receptor, keratinocyte growth factor, protein inhibitors of TNF-α, glucocorticoids, peptide analogues of glucagon-like peptide-2, glutathione peroxidase mimics, anti-sense TNF inhibitors, anti-sense ICAM-1 inhibitor, nitric oxide-releasing steroid derivatives, analogues of GLP-2, neurokinin-1 antagonists, NF-kappa-B inhibitors, orally-active phosphodiesterase IV inhibitors, thiazole derivatives, 5-lipoxygenase inhibitors, L-selectin antagonists, enzyme inhibitors, tryptase inhibitors, immunosuppressive macrolides, monoclonal antibodies against the α4β7 integrin receptor, glutathione peroxidase mimics, interferon, omega-3 fatty acids, inhibitors of cytokine synthesis, bactericidal/permeability agents, guanyl-hydrozone compounds, apoptotic antineoplastic drugs, thalidomide, recombinant interleukin-11 and mixtures thereof.

10. The method of claim 1, 6 or 9 further comprising providing infliximab, wherein the ribofuranose derivative having Formula (I) and infliximab are administered to said ubject as an admixture, separately and simultaneously, or separately in any order.

11. The method of claim 1, wherein said administration comprises parenteral administration, oral administration, inhalation, topical administration, transdermal administration, rectal administration, continuous infusion, or administration with an osmotic pump or a sustained release implant.

12. The method of claim 1, wherein said step of administering comprises orally administering the compound having Formula (I) in a dose between 100 mg and 1.5 g per day for one to four weeks.

13. The method of claim 1, wherein the step of administering comprises:
   (a) intravenously administering the compound having Formula (I) in a dose of about 10 to 40 mg/kg of body weight of the patient for about 20 to 45 minutes;
   (b) intravenously administering the compound having Formula (I) in a dose of about 5 to 25 mg/kg of body weight of the patient every six hours for four days; and
   (c) intravenously administering the compound having Formula (I) in a dose of about 2 to 15 mg/kg of body weight of the patient every six to eight hours for three days.

14. The method of claim 13, wherein the step of administering comprises:
   (a) intravenously administering the compound having Formula (I) in a dose of 33 mg/kg of body weight of the patient for 30 minutes;
   (b) intravenously administering the compound having Formula (I) in a dose of 16 mg/kg of body weight of the patient every six hours for four days; and
   (c) intravenously administering the compound having Formula (I) in a dose of 8 mg/kg of body weight of the patient every eight hours for three days.

15. The method of claim 1, wherein the disease is selected from the group consisting of pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome and Crohn's disease.

16. The method of claim 1, wherein the subject is a human.

* * * * *